United States Patent [19]

Kleinschroth et al.

[11] Patent Number: 5,043,335
[45] Date of Patent: Aug. 27, 1991

[54] INDOLOCARBAZOLES AND THE USE THEREOF

[75] Inventors: Jürgen Kleinschroth, Denzlingen; Johannes Hartenstein, Stegen-Wittental; Christoph Schächtele, Freiburg; Claus Rudolph, Vörstetten, all of Fed. Rep. of Germany

[73] Assignee: Gödecke Aktiengesellschaft, Berlin, Fed. Rep. of Germany

[21] Appl. No.: 557,299

[22] Filed: Jul. 23, 1990

[30] Foreign Application Priority Data

Jul. 25, 1989 [DE] Fed. Rep. of Germany ....... 3924538

[51] Int. Cl.$^5$ .................... C07D 498/12; A61K 31/55
[52] U.S. Cl. ..................................... 514/211; 540/545
[58] Field of Search .......................... 514/211; 540/545

[56] References Cited

U.S. PATENT DOCUMENTS 4,923,986 5/1990 Murakata et al. ................... 540/545

FOREIGN PATENT DOCUMENTS 0296110 12/1988 European Pat. Off. .............. 498/22

OTHER PUBLICATIONS

Biomedical and Biophysical Research Communications, vol. 135, No. 1, 1986, pp. 297-303; Isolation and Characterization of a Carcinoma-Associated Antigen, A. H. Ross et al.

Heterocycles, vol. 21, No. 1, 1984, pp. 309-324 Natural Product Synthesis via Cycloadditions with N-Sulfinyl Dienophiles, S. M. Weinreb et al.

The Journal of Organic Chemistry, vol. 52, No. 7, 1987 Synthesis of the Aromatic and Monosaccharide Moieties of Staurosporine, R. P. Joyce et al.

Journal of Organic Chemistry, vol. 54, 1989, pp. 824-828 Synthesis of Indolo[2,3-a]Pyrrolo[3,4-c]Carbazoles by Double Fischer Indolizations, J. Bergman et al.

Tetrahedron Letters, vol. 24, No. 13, pp. 1441-1444, 1983 Synthesis of Arcyriaflavin B, I. Hughes et al.

*Primary Examiner*—Robert T. Bond
*Attorney, Agent, or Firm*—Elizabeth M. Anderson

[57] ABSTRACT

The present invention provides 9,10,11,12-tetrahydro-9,12-epoxy-1H-diindolo [1,2,3-fg: 3',2',1'-kl]pyrrolo[3,4-i][1,6]benzodiazocine-1,3(2H)-dione and 9,10,11,12-tetrahydro-2-(tetrahydro-5-methoxy-2-furanyl) -9,12-epoxy-1H-diindolo[1,2,3-fg: 3',2',1'-kl]pyrrolo[3,4-i][1,6]benzodiazocine-1,3(2H)-dione process for the preparation thereof, pharmaceutical compositions containing the compounds, and use of the compounds in heart and blood vessel diseases such as thromboses, arterioscleroses, hypertension and inflammatory diseases, allergies, cancer and certain degenerative damage of the central nervous system, as well as diseases of the immune system.

4 Claims, No Drawings

INDOLOCARBAZOLES AND THE USE THEREOF

BACKGROUND OF THE INVENTION

Protein kinase C plays an important role in intracellular signal transduction and is closely linked with the regulation of contractile, secretory, and proliferative processes.

SUMMARY OF THE INVENTION

The present invention concerns novel compounds

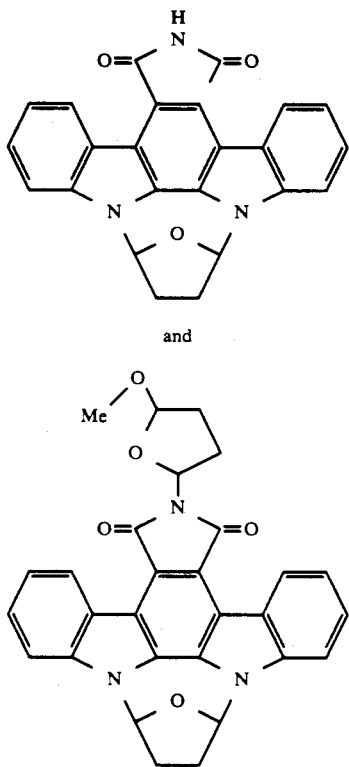

The invention also concerns pharmaceutical compositions containing these compounds in an amount effective for treating heart and blood vessel diseases. Such diseases are thromboses, arteriosclerosis, and hypertension. It also includes composition for treating inflammation, allergies, cancer, and certain degenerative damage of the central nervous system as well as diseases of the immune system.

The invention also concerns a method for treating heart and blood vessel diseases such as thromboses, arterioscleroses, and hypertension. It also includes methods for treating inflammation, allergies, cancer, and certain degenerative damage of the central nervous system as well a diseases of the immune system.

DETAILED DESCRIPTION OF THE INVENTION

The present invention is concerned with the indolocarbazole 9,10,11,12-tetrahydro-9,12-epoxy-1H-diindolo[1,2,3-fg: 3′,2′,1′,kl]pyrrolo[3,4-i][1,6]benzodiazocine-1,3(2H)-dione (I), as well as pharmaceutical compositions containing this compound and the derivative thereof substituted by a 5-methoxy-tetrahydrofuran-2-yl radical on the imide nitrogen atom, i.e., 9,10,11,12-tetrahydro-2-(tetrahydro-5-methoxy-2-furanyl) -9,12-epoxy-1H-diindolo[1,2,3-fg:-3′,2′,1′-kl]pyrrolo [3,4-i][1,6]benzodiazocine-1, 3(2H)-dione (II), obtained in the preparation of (I).

N,N-glycosides of indolocarbazoles are described in the literature as inhibitors of serine/threonine protein kinase. Staurosporin, an alkaloid glycoside of microbial origin, is compound of this class (see *Biochem. Biophys. Res. Commun.*, 135, 297/1986). A disadvantage of this very potent inhibitor is that it inhibits the various serine/threonine-specific protein kinases, such as protein kinase C and the cAMP- and cGMP-dependent protein kinases, to the same extent.

Surprisingly, it has been found that the compounds of the present invention, in contradistinction to staurosporin, display a high selectivity for protein kinase C. The compound

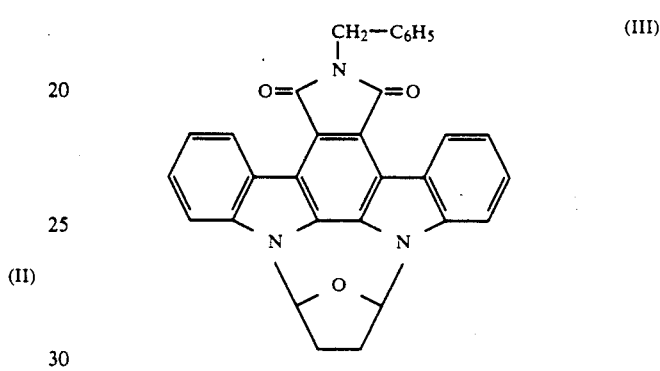

has been described in the literature. It differs from the compound of the present invention by a benzyl substituent on the imide nitrogen (see *Heterocycles*, 21, 309/1984). The literature does not disclose an inhibitory effectiveness towards protein kinases. Comparative experiments (see the following Table 1) show that under the same conditions of the in vitro enzyme assay, at a concentration of $10^{-5}$M, the compound (III) does not display a significant inhibition of protein kinase C. The extraordinary increase of potency in the case of going from the N-benzyl compound (III) to the compound (I) unsubstituted on the imide nitrogen was surprising.

The preparation of the compound of the present invention takes place by a process analogous to that described in *Heterocycles*, 21, 309/1984 by the reaction of indolo[2,3-a]pyrrolo[3,4-c]carbazole-5,7(6H)-dione

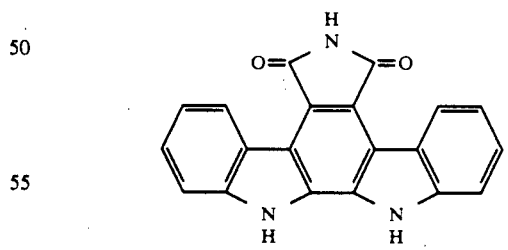

with 2,5-dimethoxytetrahydrofuran in the presence of an acidic catalyst, a halogenated hydrocarbon, for example, dichloromethane or 1,2-dichloroethane, preferably used as solvent. As catalysts, there are especially preferred p-toluenesulphonic acid and ferric chloride hexahydrate.

The synthesis of the above indolocarbazole used as starting material is described in the literature (*Tetrahedron Lett.*, 24, 1441/1983; *J. Org. Chem.* 52, 1177/1986; *J. Org. Chem.*, 54, 824/1989.

The inhibition of protein kinase C activated with phosphatidylserine and diacylglycerol was determined according to United States Patent 4,855,489, which is hereby incorporated by reference. The determination the inhibition of the cAMP- and of the cGMP-dependent protein kinase took place according to the test description below.

TABLE 1

| Compound | Inhibiton ($IC_{50}$; $\mu M$) | | | Ratio A/C | $IC_{50}$ kinase $IC_{50}$ C-Kinase G/C |
|---|---|---|---|---|---|
| | C-Kinase | A-Kinase | G-Kinase | | |
| I | 0.028 | 5.5 | 0.52 | 196 | 19 |
| Staurosporin | 0.013 | 0.04 | 0.018 | 3.1 | 1.4 |
| III | >10 | | | | |

Protein kinase C plays an important key role for the intracellular signal transduction and is closely linked with the regulation of contractile, secretory, and proliferative processes. On the basis of these properties, the compound according to the present invention can be used for the treatment of heart and od vessel diseases, such as thromboses, arterioscleroses, hypertension and inflammatory processes, allergies, cancer, and certain degenerative damage of the central nervous system, as well as of diseases of the immune system. The compound can be administered enterally or parenterally in the particularly suitable formulation in doses of 1 to 100 mg/kg of body weight and preferably of 1 to 50 mg/kg of body weight.

Description of the Test for G Kinase and A Kinase cGMP-dependent protein kinase: The enzyme was obtained from bovine lung tissue and purified and its activity determined via the incorporation of phosphorus 32-labeled phosphate into histone. The following components are contained in a test batch of 200 $\mu L$: 20 mM Tris-HCl (pH 7.4), 5 mM magnesium chloride, 1 mM DTT, 10 $\mu M$ ATP, 10 mM cGMP, 40 $\mu g$ BSA, 2% glycerol, as well as 10 $\mu g$ histone II-A and possibly the substance to be investigated. The batch is preincubated without enzyme for 4 minutes at 30° C. and the reaction started by the addition of 2.5 nM G kinase. After incubating for 5 minutes at 30° C., the reaction is stopped by the addition of 10% trichloroacetic acid and the samples then filtered off over a nitrocellulose filter. The phosphate incorporation is determined by Cerenkov counting in a scintillation counter and the percentage inhibition calculated therefrom.

cAMP-dependent protein kinase: The measurement of the activity takes place with the commercially available catalytic subunits of the enzyme. The incorporation of phosphorus 32-labeled phosphate into histone is thereby measured. A reaction batch of 200 $\mu L$ contains the following components: 50 mM PIPES-NaOH (pH 7.5), 10 mM magnesium chloride, 1 mM DTT, 40 $\mu M$ ATP, as well as 50 $\mu g$ histone H-2B. The test is carried out as in the case of G kinase. The reaction is thereby started by the addition of 6 units of the catalytic subunit of the cAMP-dependent protein kinase.

The following example is given for the purpose of illustrating the present invention:

EXAMPLE 1

9,10,11,12-Tetrahydro-9,12-epoxy-1H-diindolo[1,2,3-fg: 3',2',1'-kl]pyrrolo[3,4-i][1,6]benzodiazocine-1,3(2H)-dione A suspension of 500 mg (1.54 mMol) indolo[2,3-a]pyrrolo[3,4-c]carbazole-5,7-(6H)-dione in 25 mL dichloromethane is mixed with 3 mL (23 mMole) 2,5-dimethoxytetrahydrofuran, as well as 20 mg p-toluenesulphonic acid and stirred for 5 days at 20° C. The solvent is then distilled off and the residue partitioned between 400 mL ethyl acetate and 100 mL water. The ethyl acetate phase is separated off, dried with anhydrous sodium sulphate, and evaporated. The residue is chromatographed on silica gel with toluene/ethyl acetate (3:1 v/v). The fraction with the Rf of 0.45 is isolated and stirred with diisopropyl ether/ethyl acetate. 9,12-Epoxy-1-oxo-1H-2,3,9,10,11,12-hexahydrodiindolo[1,2,3-fg:3', 2', 1'-kl]pyrrolo [3,4-i][1,6]benzodiazocine (I) is obtained in the form of yellow crystals; mp>340° C.

As by-product, in the case of the chromatography, the derivative substituted on the imide nitrogen atom by a 5-methoxytetrahydrofuran-2-yl radical is obtained, i.e., 9,10,11,12-tetrahydro-2-(tetrahydro-5-methoxy-2-furanyl)-9,12-epoxy-1H-diindolo[1,2, 3-fg:3', 2', 1'-kl]pyrrolo [3,4-i][1,6]benzodiazocine-1,3(2H)-dione (IV); Rf 0.5 in toluene/ethyl acetate (3:1 v/v).

Spectroscopic data: MS (70 eV): m/z=393 ($M^+$, 100), 321.(26); IR (KBr):=3430, 1760, 1695, 1350, 1310, 740 $cm^{-1}$; $^1$H-NMR (DMSO-$d_6$TMS):$\delta$=2.04 (ps$\Delta$q, 2H, $CH_2$); 2.74 (m, 2H, $CH_2$); 7.33 (m, 2H, CH); 7.43 (t, 2H, J=7Hz, 8Hz, ArH); 7.63 (t, 2H, J=7Hz, 8Hz, ArH); 7.94 (d, 2H, J =8Hz, ArH); 9.01 (d, 2H, J=8Hz, ArH).

We claim:

1. A compound named 9,10,11,12-tetrahydro-9,12-epoxy-1H-diindolo[1,2,3-fg:3',2',1'-kl]pyrrolo[3,4-i][1,6]benzodiazocine-1,3(2H)-dione.

2. A compound named 9,10,11,12-tetrahydro-2-(tetrahydro-5-methoxy-2-furanyl)-9,12-epoxy-1H-diindolo[1,2,3-fg:3',2',1'-kl]pyrrolo[3,4-i][1,6]benzodiazocine-1,3(2H)-dione.

3. A pharmaceutical composition comprising a therapeutically effective amount of a compound as defined in claim 1 or claim 2 in combination with a pharmaceutically acceptable carrier.

4. A method for treating heart and blood vessel diseases which comprises administering to a mammal in need of such treatment a composition according to claim 3 in unit dosage form.

* * * * *